(12) United States Patent
Hirano et al.

(10) Patent No.: US 6,495,159 B2
(45) Date of Patent: *Dec. 17, 2002

(54) TRANSDERMAL PREPARATION CONTAINING SEROTONIN RECEPTOR ANTAGONIST

(75) Inventors: Munehiko Hirano, Tsukuba (JP); Masayoshi Maki, Tsukuba (JP); Tatsuaki Suzuki, Tsukuba (JP)

(73) Assignee: Hisamitsu Pharmaceutical Co., Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,617

(22) PCT Filed: Nov. 28, 1997

(86) PCT No.: PCT/JP97/04358

§ 371 (c)(1),
(2), (4) Date: Jun. 8, 1999

(87) PCT Pub. No.: WO98/25592

PCT Pub. Date: Jun. 18, 1998

(65) Prior Publication Data

US 2002/0102290 A1 Aug. 1, 2002

(30) Foreign Application Priority Data

Dec. 11, 1996 (JP) ............................. 8-346460

(51) Int. Cl.[7] ................. A61F 13/00; A61L 15/16; A61K 9/14
(52) U.S. Cl. ................. 424/449; 424/443; 424/448; 424/489
(58) Field of Search ................. 424/448, 449

(56) References Cited

U.S. PATENT DOCUMENTS

| | | | | |
|---|---|---|---|---|
| 5,364,628 A | * | 11/1994 | Kissel et al. | 424/448 |
| 5,486,362 A | * | 1/1996 | Kitchell et al. | 424/426 |
| 5,869,087 A | * | 2/1999 | Hirano ret al. | |
| 5,989,586 A | * | 11/1999 | Hsu et al. | |

* cited by examiner

Primary Examiner—Thurman K. Page
Assistant Examiner—Isis Ghali
(74) Attorney, Agent, or Firm—Peter F. Corless; Christine C. O'Day; Edwards & Angell, LLP

(57) ABSTRACT

A device for perutaneous treatment by a serotonin receptor antagonist, comprising at least three layers including A) a drug-impermeable backing layer, B) a drug storage layer provided between the packing layer and a drug release layer and containing serotonin receptor antagonist, and C) a drug release layer constituted of a pressure-sensitive adhesive layer capable of controlling the release of a drug.

12 Claims, 2 Drawing Sheets

TRANSDERMAL PREPARATION CONTAINING SEROTONIN RECEPTOR ANTAGONIST

FIELD OF THE INVENTION

This invention relates to an apparatus for administering a vomiting depressant at the time of chemotherapy of cancer. More particularly, this invention relates to a percutaneous therapeutic apparatus which enables to control ooze of liquid medicine from a drug storage layer during preservation of the apparatus by laminating a pressure-sensitive adhesive for controlling ooze of medicine to a drug releasing surface, and to a percutaneous therapeutic apparatus containing serotonin-receptor antagonist which is characterized by enabling to administer the predetermined amount of the serotonin-receptor antagonist precisely and certainly to a patient.

BACKGROUND OF THE INVENTION

In a field of percutaneous therapeutics, a percutaneous therapeutic apparatus such as Estraderm, Nitorderm and so forth have been conventionally developed and used clinically. However, in these conventional apparatuses, in the case of, for example, Estraderm, there occur that adhesion of the apparatus to skin decreases due to an interaction with medicine during preservation. Such decline of adhesion of a patch medicine during administration causes a decline of area for absorbing medicine and there is a case where blood concentration of drug sufficient for therapeutics can not be obtained, which may be possibly a deadly problem to the patch medicine. Several percutaneous therapeutic apparatuses have been proposed in which a medicine releasing surface and a pressure-sensitive adhesive layer having to do with adhesion to skin are separated.

For example, Unexamined Patent Publication (Kokai) No.61-265150 discloses an example in which a medicine storage layer is separated from an adhesive existing on the outer periphery of the medicine storage layer by a circumferential se. The percutaneous therapeutic apparatuses described in examples disclosed in Unexamined Utility Model Publication (Kokai) No, 60-63344, Unexamined Utility Model Publication (Kokai) No. 62-182942, Unexamined Patent Publication (Kokai) No. 62-195326, Unexamined Patent Publication (Kokai) No1-224312, Examined Patent Publication (Kokoku) No. 4-46592, Japanese National Publication No. 6-503252, Unexamined Patent Publication (Kokai) No.-1283 and Unexamined Patent Publication (Kokai) No. 62-212320 are common to Unexamined Patent Publication (Kokai) No. 61-265150 on the point that an interaction of the pressure-sensitive adhesive layer on the periphery of the medicine releasing surface with the medicine storage layer are disconnected.

However, when such pressure sensitive adhesive layers as described in these examples are placed to the periphery of the medicine-releasing surface, the apparatus as a whole is bulky and, as a result, adhesion to skin lowers. There is a fear of increase in skin irritation in cases where the area of the pressure sensitive adhesive is enlarged in order to rise the adhesion or adhesive force.

On the other hand while serotonin ($5\text{-}HT_3$)-receptor antagonist which is used as antiemetic for inhibiting vomiting which occurs often at the time of administration of cancer chemotherapeutic is used in therapeutics by oral administration and so forth, the control of blood concentration of drug is difficult and there occurs a problem that side effect on extrapyramidal motor system. In recent years, developments of a patch medicine have been tried in order to solve these problems as proposed in, for example, Examined Patent Publication (Kokoku) No. 5-79646 and so forth which, however, encounter a problem of adhesion to skin and which hardly exhibit sufficient drug efficacy. And, a patch medicine in which butyrophenone-group drug is contained in acrylic ester polymer base is proposed in Unexamined Patent Publication (Kokai) No. 8-113533. However, an acrylic type pressure-sensitive adhesive is low in its drug releasing property and has a strong irritation to skin, and, it is no, therefore, equal to long-term continuous administration. And, there is fear that these pharmaceutical preparations the release of which is not controlled rise blood concentration temporarily because of rapid rising of initial release and increase an occurrence of side effect.

DISCLOSURE OF THE INVENTION

The problems to be solved by this invention are to get rid of lowering of adhesion resulted from an interaction of an apparatus with medicine during preservation of the apparatus and increase of skin irritation accompanying with enlargement of bulk caused by placing a pressure-sensitive adhesive layer on the periphery.

And, this invention relates to an apparatus for supplying to skin surface an effective amount of serotonin-receptor antagonist for therapeutics from a liquid medicine storage layer through a medicine releasing layer and, more particularly, relates to a percutaneous therapeutic apparatus the medicine-releasing surface of which is sealed to make a loss in medicine substantially zero when using the apparatus and which is able to apply to a patient the predetermined amount of the serotonin-receptor antagonist precisely and certainly.

Inventors of this invention have made devotedly many researches and developments in order to solve the aforementioned problems. As a result, we have discovered that release of drug can be controlled and simultaneously medicine can be prevented from oozing by making use of a medicine-releasing layer comprising a pressure-sensitive adhesive layer which is able to control the release of drug in a percutaneous therapeutic apparatus. That is to say, according to the percutaneous therapeutic apparatus of this invention having a medicine-releasing layer comprising a pressure-sensitive adhesive layer which is able to control release of the drug, good adhesion can be obtained and increase of skin irritation resulted from enlarged bulk can be prevented and, simultaneously, ooze of the medicine can be prevented during preservation and an effective amount of the medicine for therapeutics can be released precisely and certainly from the present apparatus after sticking the present apparatus on skin of a patient.

That is to say, this invention provides a percutaneous therapeutic apparatus which enables;
(1) to control release of medicine by a simple structure,
(2) to improve preservation-stability of medicine,
(3) to lower irritation to skin,
(4) to obtain good adhesion to skin,
(5) to obtain high cohesive force of a pressmen sensitive adhesive.

This invention relates to a percutaneous therapeutic apparatus having at least three layers comprising;
(A) a medicine non-permeable backing layer,
(B) a medicine storage layer containing serotonin-receptor antagonist between the backing layer and a medicine-releasing layer, (C) a pressure-sensitive layer which is able to control release of medicine.

The percutaneous therapeutic apparatus of this invention can be provided with a release liner layer which is able to be released when using outside the aforementioned medicine-releasing layer. And, the medicine-releasing layer of this invention which controls the release of medicine can include a medicine-permeable film (hereinafter, sometimes referred to as porous layer) other than for the pressure-sensitive adhesive layer.

Further, the invention also provides a percutaneous-absorption pharmaceutical preparation containing serotonin-receptor antagonist which can be administered stably over a long period of times.

More in detail, this invention provides a percutaneous therapeutic apparatus having a medicine-releasing layer containing a pressure-sensitive adhesive layer enabling to control release of drug comprising pressure-sensitive adhesive containing rubber elastomer, tackifier resin and softening agent or pressure-sensitive adhesive further containing acrylic type pressure-sensitive adhesive other than these components.

Further more in detail, the pressure-sensitive adhesive layer of this invention is prepared by applying the aforementioned pressure-sensitive adhesive to whole area of the medicine-releasing surface.

DESCRIPTION OF THE MOST PREFERRED EMBODIMENT FOR WORKING THE INVENTION

Figure 1:
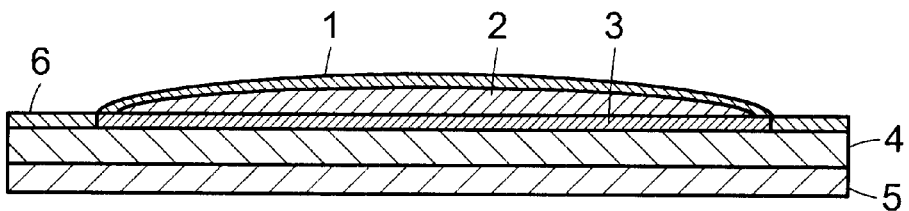
FIG. 1 is a cross section showing a structure of layers of a working embodiment of the percutaneous therapeutic apparatus of this invention.

A percutaneous therapeutic apparatus having a layer structure shown in FIG. 1 can be given as one embodiment of the percutaneous therapeutic apparatus of this invention.

In FIG. 1, liquid medicine containing a therapeutically effective amount of drug components is encapsulated in a medicine storage layer 2 between the backing layer 1 and a porous material 3 of a medicine-permeable film. A pressure-sensitive adhesive layer 4 is laminated to outer layer of porous material 3 and coated with a release liner 5 for sealing medicine, which release liner 5 is released when using this invention.

Figure 2:
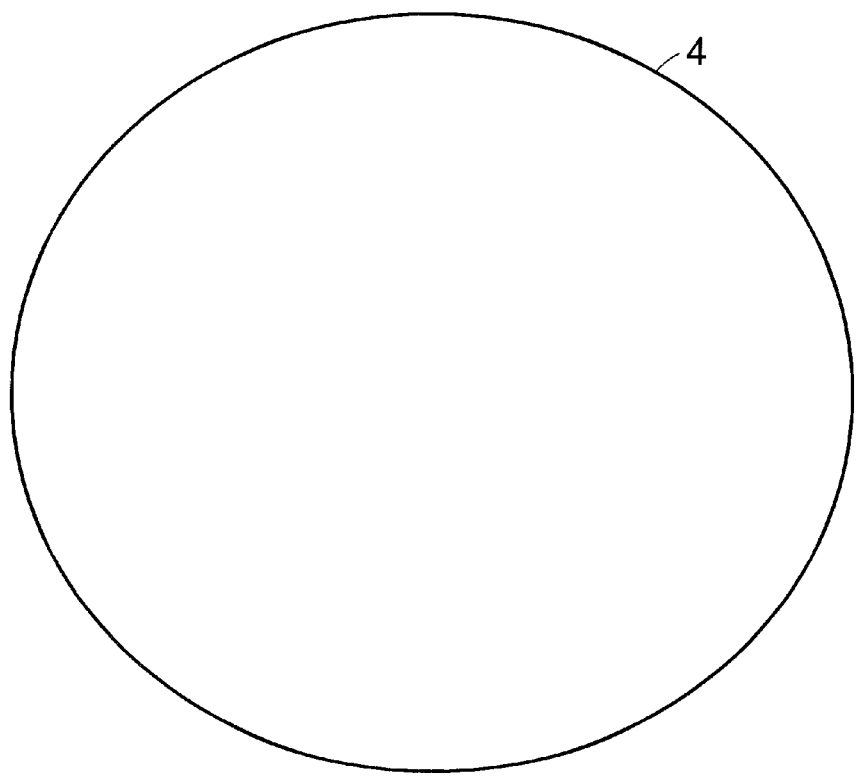
FIG. 2 shows a state as seen from skin when removing a release liner of a working embodiment of the percutaneous therapeutic apparatus of this invention.

FIG. 2 is a view of a state as seen from the side of skin when removing a release liner 5 of the percutaneous therapeutic apparatus of this invention The press layer 6 is pressed somewhat deeply along the outer periphery of the effective releasing surface at the portion where the medicine permeable film and the backing material are sealed in order to seal the medicine storage layer 2. Since the medicine is not stored between the release liner 5 and the pressure-sensitive adhesive layer 4 by virtue of the presence of the pressure-sensitive adhesive layer 4, there is no chance for loss in medicine when releasing the release liner 5. When the apparatus of this invention is applied to skin of a patient, the medicine can be released from the medicine-releasing layer 3.

The drug contained in the medicine storage layer of the apparatus of this invention is serotonin-receptor antagonist, and may be preferable antagonist for $5-T_3$ and/or $5-HT_4$ receptor, one of sub-types of serotonin-receptor which is used as antiemetic in order to control vomiting occurring often when administering chemotherapeutics for cancer chemothrapy. As serotonin-receptor antagonist of this invention may be exemplified by a serotonin-receptor antagonist such as granisetron hydrochloride, azasetron hydrochloride, ondansetron hydrochloride, lamosetron hydrochloride (the above names are general names), (+)-8,9-dihydro-10-methyl-7-[(5-methyl-4-imidazolyl) methyl] pyrido [1,2-a] indole-6 (7H)-on hydrochloride, (R)-5-(2,3-dihydro-1H-indole-1-ilcarbonyl)-4,5,6,7-tetrahydro-1-benzimdazole-hydrochloride, End-N-(3,9-dimethyl-3,9-diazabicyclo [3,3,1] none-7-il)-1H-indazole-3-carboxyamide dibasic acid salt (the above names are chemical names) and so forth. These serotonin-receptor antagonists may be in a state of liberation or pharmaceutically acceptable organic or inorganic salt. The compounding amount of the serotonin-receptor antagonist is sufficient amount effective for therapeutics, and may be preferable, for example, 0.1–10 weight percent. And, the combined-use of more than two kids of these medicines may be acceptable, if necessary.

The aforementioned us of this invention are preferably formed in a state of liquid or semisolid (ointment) by adding the other components thereto and stared in the medicine storage layer. As to the base composition for preparing liquid medicine of the percutaneous therapeutic apparatus of this invention, the compounding ratio of water may be preferably 20–70 weight percent and the compounding ratio of lower alcohol may be preferably 10–40 weight percent. The compounding ratio of absorption enhancer such as aliphatic alcohol and so forth may be preferably 0.1–10 weight percent. The compounding ratio of wetting agent such as glycerine, polyethylene glycol and so forth may be preferably 20–40 weight percent. The compounding ratio of irritation-reducing agent such as glycerol monooleate or glycerol monolaurate or mixture thereof may be preferably 1–10 weight percent These bases are properly formulated within each compounding ratio.

The absorption enhancer used in this invention may be preferable aliphatic acid, aliphatic alcohol or ester of aliphatic acid having 7–20 carbon atoms, and, above all lauryl alcohol and myristyl alcohol may be more preferable since they exhibit high absorption enhancer property and relatively poor irritation to skin As a wetting agent may be preferable sorbitol, polyethylene glycol, diglycerin, propylene glycol, butylene glycol dipropylene glycol, sodium pyrrolidone carboxylate, ethyl carbitol, D-xylitol, glycerin, hyaluronic acid, and, above all, glycerin or polyethylene glycol may be particularly preferable. The water component may be preferable buffer solution As the irritation-reducing agent may be preferable ester of aliphatic add or ester of sorbitol aliphatic acid or mixture thereof As lower alcohol may be preferable particularly ethanol or isopropanol.

And, gelling agent may be added to these components if necessary. As the proper gelling agent to be used may be exemplified by carboxyvinyl polymer, sodium polyacrylic acid, polyvinyl pyrrolidone, hydroxydipropylmethyl cellulose, hydroxyethyl cellulose, hydroxypropyl cellulose, methyl cellulose, carboxymethyl cellulose. Additives such as ultraviolet-absorbing agent, anti-oxidant, antiseptic and so forth may be added, if necessary. For example, as the ultraviolet-absorbing agent may be exemplified by publicly-known para-aminobenzoic acid derivatives, antic acid derivatives, salicylic acid derivatives, coumalic acid derivatives, amino acid derivatives, benzotriazole derivatives, tetrazole derivatives, imidazoline derivatives, pyrimidine derivatives, dioxane derivatives, ran derivatives, pyrone derivatives, camphor derivatives, nucleic acid derivatives, allantoin derivatives, nicotinic acid derivatives, shikonin or vitamin-6 derivatives, and benzophenone derivatives such as 2-hydroxy-4-methoxybenzophenone derivatives and so forth may be more preferably used. As the antioxidant may be exemplified by ascorbic acid, ester of stearic acid, sodium ascorbate, tocopherol (d-form, 1-form, d, 1-form of α-tocopherol, β-tocopherol, γ-tocopherol, δ-tocopherol and so forth) and ester derivatives thereof, nordihydroguaceretic acid, dibutylhydroxytoluene, butylhydroxyanisole, tort-butylhydroxynon, ester of Gallic acid (ester of ethyl, propyl, isoamyl and so forth) 1-oxo-3-methyl-4-isopropylbenzene.

Next, the backing layer is explained. The film for the backing layer should be excellent in so-called barrier properties in order to prevent ooze and vaporization of medicine and should have such properties as to be easily bonded to porous material of the medicine-releasing layer. And, it is also preferable that the film for the backing layer has modest softness when the apparatus of this invention is stuck to skin. The material of the backing layer is not particularly limited even if it has the aforementioned requirements and may be exemplified by aluminum, ethylene-vinylacetate copolymer or saponified products thereof, cellulose acetate, cellulose, Nylon, polyester, polyethylene, polyvinylidene chloride, polycarbonate, polyvinylalcohole, polypropylene. In order to improve the barrier properties, adhesion to the medicine-releasing layer and so forth, these materials may be used in a form of a film, or in a form of a laminated film prepared by laminating these materials in a form of paper or cloth to a film, or may be used after being deposited with aluminum or ceramic thereon.

A preferred example of the composition usable in this invention is illustrated. The materials constituting the medicine-releasing film is porous and may be exemplified by ethylene-vinylacetate copolymer, cellulose, cellulose acetate, polyester, polyethylene, polypropylene and so forth. The porous materials have preferably 10–500 sec/100 cc of Gurley permeability.

It is preferable that the pressure-sensitive adhesive layer which is able to control release of medicine has sufficient adhesive force to attach the apparatus of this invention to skin. The pressure-sensitive adhesive layer of this invention makes use of preferably pressure-sensitive adhesive comprising rubber elastomer, tackifier resin and softening agent, or pressure-sensitive adhesive further containing acrylic type pressure-sensitive adhesive other than these three components. It is preferable that the pressure-sensitive adhesive layer of this invention is prepared by applying the aforementioned pressure-sensitive adhesive to whole area of the medicine-releasing layer. As the rubber elastomer may be preferably exemplified by polyisobutylene (for example, polyisobutylene available from Exxon Chemicals as trade name "Vistanex" or from BASF as trade name "Oppano 1"), (A–B) n-Type elastic polymer (for example, styrene-butadiene-styrene block copolymer available from Shell Chemicals as trade name "Cariflex TR-1101"), styrene-isoprene styrene block copolymer (available from Shell Chemicals as trade name "Cariflex R-1107", "Cariflex TR-1111"), styrene-isoprene-styrene block copolymer (available from Japan Synthetic Rubber co., Ltd. as trade name "JSR 5000", "JSR 5100"), styrene-isoprene-styrene block copolymer (available from Nippon Zeon Co., Ltd. as trade name "Quin tack 3421"). These rubber elastomers may be used singly or in combination with more than one of them, and the combined-use of polyisobutylene and styrene-isoprene-styrene block copolymer fay be preferable.

The compounding ratio of the rubber elastomer in the pressure-sensitive adhesive may be 5–50 weight percent, preferably 10–40 weight percent, more preferably 10–30 weight percent. As the tackifier resin, a component of the pressure-sensitive adhesive, may be exemplified by alicyclicsaturated hydrocarbon resin (for example, "Arcon P-100" (trade name), rosin ester (for example, "KE-311", "KE-100" (trade name), "Super Ester S-100" (trade name), hydrogenated petroleum resin (for example, "Foral 105" (trade name), terpene-series hydrogenated petroleum resin (for example, "Cryalone P-105" (trade name). The compounding ratio of the tackifier resin in the pressure-sensitive adhesive maybe 5–50 weight percent, preferably 5–40 weight percent, more preferably 10–35 weight percent.

The softening agent, a component of the pressure-sensitive adhesive, may be exemplified by liquid paraffin polybutene, castor oil, cottonseed oil, palm oil coconut oil, process oil The compounding ratio of the softening agent in the pressure-sensitive adhesive may be 10–70 weight percent, preferably 15–60 weight percent, more preferably 20–50 weight percent.

An acrylic adhesive which is able to be used simultaneously with the rubber elastomer as a component for the pressure-sensitive adhesive may be preferably, particularly, homopolymer of (meth) acrylic acid alkyl ester having alkyl group having 4–18 carbon atoms, or copolymer thereof or copolymer of the above-mentioned (meth) acrylic acid alkyl ester and the other functional monomer. As the above-mentioned (meth) acrylic acid alkyl ester may be exemplified by butyl acrylate, isobutyl acrylate, hexyl acrylate, octyl acrylate, 2-ethylhexyl acrylate, iso-octyl acrylate, decyl acrylate, iso-decyl acrylate, lauryl acrylate, stearyl acrylate, methyl methacrylate, ethyl methacryate, butyl methacryate, iso-butyl methacrylate, 2-ethylhexyl methacryate, iso-octyl methacryate, decyl methacryate, iso decyl methacryate, lauryl methacrylate, stearyl methacryate. The above-mentioned functional monomer may be exemplified by monomer having a hydroxyl group, monomer having a carboxyl group, monomer having an amide group, a monomer having an amino group, a monomer having a pyrrolidone ring. The monomer having a hydroxyl group may be exemplified by hydroxyalkyl (meth) acrylate such as 2-hydroxyethyl (meth) acrylate, hydroxypropyl (meth) acrylate and so forth. The monomer having a carboxyl group maybe exemplified by α,β-unsaturated carboxylic acid such as acrylic acid, methacrylic acid and so forth, ester of maleic acid and monoalkyl such as butyl maleate and so forth, maleic acid, fumaric acid, crotonic acid. Maleicanhydride is also a component for copolymer similarly to maleic acid The monomer having an amide group may be exemplified by alkyl (meth) acrylic amide such as acrylic amide, dimethylacryfic amide, diethylacrylic amide and so forth, N-alkoxymethyl (meth) acrylic amide such as N-butoxymetylacrylic amide, N-ethoxymetylacrylic amide and so forth, diacetonacrylic amide. The monomer having an amino group may be exemplified by dimethylaminoethylacrylate and so forth. The monomer having a pyrrolidone ring may be exemplified by N-vinyl-2-pyrrolidone. The compounding ratio of the acrylic type pressure-sensitive adhesive may be 0–80 weight percent (means 0 weight percent in the case of single use of rubber elastomer), preferably 5–60 weight percent, more preferably 10–30 weight percent.

The film thickness of the pressure-sensitive adhesive layer may be preferably 30–300 μm, and a problem occurs in adhesion when it is thinner than 30 µm, and, in contrast, there occurs a case where the control of release is difficult when it is thicker than 300 µm.

The percutaneous therapeutic apparatus having safety to skin and release control containing serotonin (5-$HT_3$ and/or 5-$HT_4$)-receptor antagonist of this invention is prepared by combination of these elastomer, tackifier resin, softening agent and/or acrylic type pressure sensitive adhesive.

And, well-known additives may be added, if necessary, to the pressure-sensitive adhesive layer of this invention for adjustment of adhesive, safety and stability, more concretely, water-absorbing polymer such as "SUMIKA-GEL SP-520" (trade name), "AQUA KEEP 4 SH" (trade name), "ARASOAP 800 F" (trade name), "SUNWET 1M-1000 HPS" (trade name), inorganic additives such as zinc oxide, calcium carbonate, titanium dioxide, silica, solubilizer such as polyethylene glycol, crotamiton may be added properly in a suitable amount.

The film constituting the release liner layer has to prevent ooze or vaporization of medicine from the medicine-releasing layer during the preservation of the apparatus of this invention, an the release liner layer should be removed when using the apparatus. As the material of the release liner film may be used aluminum, cellulose, polyester, polyethylene, polypropylene and so forth, which may be used in a form of a laminated film thereof if necessary. And, it is not objectionable that releasability or barrier property is adjusted by treating the surface of the material of the release liner film with silicon or fluorocarbon or by adding well-known additives to the material of the liner. The release liner may be provide with a lug for releasing in order to make handling when releasing easy. With respect to the adhesion between the medicine-releasing layer and the release liner covering thereon, the medicine-releasing layer and the release liner covering thereon should be bonded each other during the preservation of the apparatus, and such release liner has to be released to remove when using the apparatus. Therefore, the adhesive force between the medicine releasing layer and the release liner covering thereon must be lower that that of between the backing layer and the medicine-releasing layer.

The form of the apparatus is not particularly restricted, but may be exemplified by circle, ellipse, polygon. The area of the apparatus may be preferably 1 $cm^2$-200 $cm^2$. In the case where the area is narrower than 1 $cm^2$, it is difficult to release the release liner to stick on skin, and in the case where the area is larger than 200 $cm^2$, the feel of wearing is bad. On the contrary, the thickness of the apparatus may be preferably 0.1–15 mm in overall thickness of the apparatus including the release liner. In the case where the thickness is thinner than 0.1 mm, since the amount of medicine to be administered per the medicine-releasing area is unavoidably diminished and the persistency of releasing the medicine is shortened, it is not preferable. In the case where the thickness is thicker than 15 mm, since there is high possibility that the apparatus is removed by unexpected action of a patient, it is not preferable.

Since the percutaneous therapeutic apparatus of this invention thus prepared has a structure in which the medicine is encapsulated between the backing layer and the medicine-releasing layer, it can accept any medicine having a wide range of viscosity from liquid-state medicine of low viscosity to that of high viscosity and it has the merit for preferable design of the safety, stability and effectiveness because it has a wide range of selection of the composition of medicine compared with a tape-medicine and so forth.

The method of preparing the percutaneous absorption medicine of this invention is not particularly restricted, but any conventional method can be adopted. For example, according to the method of preparation of the medicine-releasing layer of this invention, every component of the pressure-sensitive adhesive layer is dissolved in an organic solvent such as hexane, toluene, ethyl acetate, ad thereafter spread on the release liner to remove the organic solvent. The pressure-sensitive adhesive layer opposite to the release liner is coated with a porous material to prepare the medicine-releasing layer which is then cut to desired form, and 0.5 g of medicine prepared independently are added dropwise to the side of the porous material which is then heat-sealed with the backing layer and thereafter cut along the outer periphery of the heat-seal, thereby, the percutaneous therapeutic apparatus of this invention can be obtained And, the medicine which is able to be stored in the percutaneous absorption pharmaceutical composition can be prepared by treating properly lower alcohol, wetting agent water, irritation-reducing agent, absorption enhancer and medicine to prepare by means of emulsification testing machine (NIKKO CHEMICAL ET-3A).

This invention is explained in greater detail in the following examples, comparative examples and test examples, which are illustrative and not to be taken as limiting of this invention. Numerical values with respect to amount of components described in examples, comparative examples and test examples are on the basis of weight percent.

Example 1

| Composition of the pressure-sensitive adhesive | |
| --- | --- |
| styrene-isoprene-styrene block copolymer | 10.5 |
| acrylic type pressure-sensitive adhesive (2-ethylhexyl acrylate/vinyl acetate copolymer) | 10.0 |
| liquid paraffin | 49.3 |
| tackifier (alicyclicsaturated hydrocarbon resin) | 20.0 |
| polyisobutylene | 10.0 |
| dibutyl hydroxytoluene | 0.2 |

The pressure-sensitive adhesive was prepared from the above-described formulation m accordance with the aforementioned method and laminated with porous material, thereafter was cut to desired shape to form a medicine-releasing layer.

| Composition of medicine | |
| --- | --- |
| ethanol | 24.0 |
| buffer water solution | 40.0 |
| glycerin | 25.0 |
| lauryl alcohol | 0.5 |
| glycerin monooleate | 3.0 |
| sorbitan monolaurate | 1.0 |
| sodium carboxymethylcellulose | 3.5 |
| ondansetron hydrochloride | 3.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 2

| Composition of the pressure-sensitive adhesive | |
|---|---|
| styrene-isoprene-styrene block copolymer | 30.0 |
| acrylic type pressure-sensitive adhesive (2-ethylhexyl acrylate/ethyl acrylate-vinyl acetate copolymer) | 5.0 |
| liquid paraffin | 30.5 |
| tackifier (alicyclic saturated hydrocarbon resin) | 25.0 |
| polyisobutylene | 5.0 |
| polyethylene glycol 200 | 4.0 |
| dibutyl hydroxytoluene | 0.5 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 40.5 |
| polyethylene glycol 300 | 25.0 |
| lauryl alcohol | 0.5 |
| glycerin monooleate | 3.0 |
| sorbitan monolaurate | 1.0 |
| hydroxypropylmethylcellulose 4000 | 2.0 |
| azasetron hydrochloride | 4.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 3

| Composition of the pressure-sensitive adhesive | |
|---|---|
| styrene-isoprene-styrene block copolymer | 15.0 |
| acrylic type pressure-sensitive adhesive (2-ethylhexyl acrylate/vinyl pyrrolidone copolymer) | 11.5 |
| liquid paraffin | 14.5 |
| tackifier (rosin ester) | 35.0 |
| polyisobutylene | 15.0 |
| crotamiton | 5.0 |
| sunwet 1 M–1000 MPS | 3.0 |
| dibutyl hydroxytoluene | 1.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 41.5 |
| polyethylene glycol 400 | 25.0 |
| lauryl alcohol | 0.5 |
| glycerin monooleate | 3.0 |
| sorbitan monolaurate | 1.0 |
| hydroxypropylmethylcellulose 4000 | 2.0 |
| ondansetron hydrochloride | 3.0 |

1.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 4

| Composition of the pressure-sensitive adhesive | |
|---|---|
| styrene-isoprene-styrene block copolymer | 20.0 |
| acrylic type pressure-sensitive adhesive (acrylic acid/octyl acrylate copolymer) | 20.0 |
| liquid paraffin | 34.5 |
| tackifier (alicyclic saturated hydrocarbon resin) | 17.0 |
| polyisobutylene | 8.0 |
| diibutyl hydroxytoluene | 0.5 |

The pressure-sensitive adhesive was prepared from the above described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 40.0 |
| polyethylene glycol 300 | 26.0 |
| myristyl alcohol | 1.0 |
| glycerin monooleate | 2.0 |
| hydroxypropylmethylcellulose 4000 | 2.0 |
| lamosetron hydrochloride | 5.0 |

0.5 g of the above described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 5

| Composition of the pressure-sensitive adhesive | |
|---|---|
| styrene-isoprene-styrene block copolymer | 25.0 |
| liquid paraffin | 42.0 |
| tackifier (alicyclic saturated hydrocarbon resin) | 20.0 |
| polyisobutylene | 8.0 |
| polyethylene glycol 200 | 4.0 |
| diibutyl hydroxytoluene | 1.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 25.0 |
| buffer water solution | 41.0 |
| polyethylene glycol 300 | 25.0 |
| myristyl alcohol | 1.0 |
| sorbitan monolaurate | 1.0 |
| hydroxy propylmethyl cellulose 4000 | 2.0 |
| glanisetron hydrochloride | 5.0 |

0.5 g of the above described medicine were added dropwise to the side of the porous material which was then heatsealed with a backing layer to form a heatsealed laminate. And, thereafter the heatsealed laminate was cut along the outer periphery of the heatsealed portion to obtain the perutaneous therapeutic apparatus of this invention.

Example 6

| Composition of the pressure-sensitive adhesive | |
|---|---|
| styrene-isoprene-styrene block copolymer | 12.0 |
| acrylic type pressure-sensitive adhesive (2-ethylhexyl acrylate / vinyl acetate copolymer) | 15.0 |
| liquid paraffin | 17.8 |
| tackifier (rosin ester) | 33.0 |
| polyisobutylene | 15.0 |
| crotamiton | 5.0 |
| sunwet 1M-1000 MPS | 1.0 |
| diibutylhydroxytoluene | 1.2 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| isopropanol | 40.0 |
| buffer water solution | 20.0 |
| polyethylene glycol 400 | 30.0 |
| myristyl alcohol | 1.0 |
| sorbitan monolaurate | 2.0 |
| hydroxy propylmethyl cellulose 4000 | 2.0 |
| azasetron hydrochloride | 5.0 |

0.5 g of the above described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 7

| Composition of the pressure-sensitive adhesive | |
|---|---|
| styrene-isoprene-styrene block copolymer | 12.0 |
| acrylic type pressure-sensitive adhesive | 5.5 |
| (2-ethylhexyl acrylate / methyl acrylate copolymer) | |
| liquid paraffin | 23.0 |
| tackifier (alicyclic saturated hydrocarbon resin) | 50.0 |
| polyisobutylene | 8.0 |
| diibutyl hydroxytoluene | 1.5 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 10.0 |
| buffer water solution | 61.0 |
| polyethylene glycol 400 | 20.0 |
| lauryl alcohol | 1.0 |
| sorbitan monolaurate | 2.0 |
| hydroxy propylmethyl cellulose 4000 | 2.0 |
| ondansetron hydrochloride | 4.0 |

05 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 8

| Composition of the pressure-sensitive adhesive | |
|---|---|
| styrene-isoprene-styrene block copolymer | 10.0 |
| acrylic type pressure-sensitive adhesive (2-ethylhexyl acrylate / vinyl pyrrolidone copolymer) | 30.0 |
| liquid paraffin | 29.0 |
| tackifier (alicyclic saturated hydrocarbon resin) | 20.0 |
| polyisobutylene | 10.0 |
| diibutyl hydroxytoluene | 1.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 40.0 |
| glycerine | 25.0 |
| lauryl alcohol | 0.5 |
| glycerine monooleate | 3.0 |
| sorbitan monolaurate | 1.0 |
| sodium carboxydimethyl cellulose 4000 | 3.5 |
| Lamosetron hydrochloride | 3.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 9

| Composition of the pressure-sensitive adhesive | |
|---|---|
| styrene-isoprene-styrene block copolymer | 30.0 |
| acrylic type pressure-sensitive adhesive (2-ethylhexyl acrylate / vinyl acetate copolymer) | 10.0 |
| liquid paraffin | 20.0 |
| tackifier (alicyclic saturated hydrocarbon resin) | 29.5 |
| polyisobutylene | 5.0 |
| polyethylene glycol 200 | 5.0 |
| diibutyl hydroxytoluene | 0.5 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 40.5 |
| polyethylene glycol 300 | 25.0 |
| lauryl alcohol | 0.5 |
| glycerine monooleate | 3.0 |
| sorbitan monolaurate | 1.0 |
| hydroxy propylmethyl cellulose 4000 | 2.0 |
| lamosetron hydrochloride | 4.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 10

| Composition of the pressure-sensitive adhesive | |
|---|---|
| styrene-isoprene-styrene block copolymer | 15.0 |
| acrylic type pressure-sensitive adhesive (2-ethylhexyl acrylate / octyl acrylate copolymer) | 15.0 |
| liquid paraffin | 14.0 |
| tackifier (alicyclic saturated hydrocarbon resin) | 35.0 |
| polyisobutylene | 15.0 |
| crotamiton | 3.0 |
| sunwet 1M-1000 MPS | 2.0 |
| dibutyl hydroxytoluene | 1.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 40.0 |
| polyethylene glycol 400 | 25.0 |
| lauryl alcohol | 0.5 |
| glycerine monooleate | 3.0 |
| sorbitan monolaurate | 1.0 |
| hydroxypropylimethyl cellulose 4000 | 2.0 |
| ondansetron hydrochloride | 4.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 11

| Composition of the pressure-sensitive adhesive | |
|---|---|
| styrene-isoprene-styrene block copolymer | 21.0 |
| acrylic type pressure-sensitive adhesive (2-ethylhexyl acrylate / vinyl acetate copolymer) | 2.0 |
| liquid paraffin | 31.0 |
| tackifier (alicyclic saturated hydrocarbon resin) | 16.0 |
| polyisobutylene | 29.0 |
| dibutyl hydroxytoluene | 1.0 |

The pressure sensitive adhesive was prepared from the above-described formulation in accordance with the aforementioned method and laminated with porous material, thereafter was cult to desired shape to form a medicine-releasing layer.

| Composition of medicine | |
|---|---|
| ethanol | 20.0 |
| buffer water solution | 40.0 |
| polyethylene glycol 300 | 30.0 |
| myristyl alcohol | 1.0 |
| glycerine monooleate | 2.0 |
| hydroxypropylmethyl cellulose 4000 | 2.0 |
| ondansetron hydrochloride | 5.0 |

0.5 g of the above described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 12

| Composition of the pressure-sensitive adhesive | |
|---|---|
| styrene-isoprene-styrene block copolymer | 14.0 |
| acrylic type pressure-sensitive adhesive (2-ethylhexyl acrylate / vinyl pyrrolidone copolymer) | 5.0 |
| liquid paraffin | 70.0 |
| tackifier (alicyclic saturated hydrocarbon resin) | 10.0 |
| dibutyl hydroxytoluene | 1.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 24.0 |
| buffer water solution | 41.0 |
| polyethylene glycol 300 | 25.0 |
| myristyl alcohol | 2.0 |
| sorbitan monolaurate | 1.0 |
| hydroxypropyl methylcellulose 4000 | 2.0 |
| azasetron hydrochloride | 5.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 13

| Composition of the pressure-sensitive adhesive | |
|---|---|
| styrene-isoprene-styrene block copolymer | 5.0 |
| acrylic type pressure-sensitive adhesive (2-ethylhexyl acrylate / methyl acrylate copolymer) | 80.0 |
| liquid paraffin | 10.0 |
| tackifier (alicyclic saturated hydrocarbon resin) | 5.0 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| isopropanol | 40.0 |
| buffer water solution | 20.0 |
| polyethylene glycol 400 | 30.0 |
| myristyl alcohol | 1.0 |
| sorbitan monolaurate | 2.0 |
| hydroxypropyl methylcellulose 4000 | 2.0 |
| glanisetron hydrochloride | 5.0 |

0.5 g of the above described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

Example 14

| Composition of the pressure-sensitive adhesive | |
|---|---|
| styrene-isoprene-styrene block copolymer | 20.0 |
| acrylic type pressure-sensitive adhesive (2-ethylhexyl acrylate vinyl / acetate copolymer) | 13.5 |
| liquid paraffin | 23.0 |
| tackifier (alicyclic saturated hydrocarbon resin) | 34.0 |
| polyisobutylene | 8.0 |
| dibutyl hydroxytoluene | 1.5 |

The pressure-sensitive adhesive was prepared from the above-described formulation in accordance with the aforementioned method and laminated with porous material, thereafter was cut to desired shape to form a medicine-releasing layer.

| Composition of medicine | |
|---|---|
| ethanol | 10.0 |
| buffer water solution | 61.0 |
| polyethylene glycol 400 | 20.0 |
| lauryl alcohol | 1.0 |
| sorbitan monolaurate | 2.0 |
| hydroxypropyl methylcellulose 4000 | 2.0 |
| azasetron hydrochloride | 4.0 |

0.5 g of the above-described medicine were added dropwise to the side of the porous material which was then heatsealed with a backing layer to form a heatsealed laminate. And, thereafter the heatsealed laminate was cut along the outer periphery of the heatsealed portion to obtain the percutaneous therapeutic apparatus of this invention.

[Comparative Example]
Comparative Example 1

| Pressure-sensitive adhesive | |
|---|---|
| acrylic type pressure-sensitive adhesive (TS-620; Nippon Carbide Co., Ltd.) | |
| Composition of medicine | |
| ethanol | 24.0 |
| buffer water solution | 40.0 |
| glycerine | 25.0 |
| lauryl alcohol | 0.5 |
| glycerine monoleate | 3.0 |
| sorbitan monolaurate | 1.0 |
| sodium carboxymethylcellulose | 3.5 |
| ondansetron hydrochloride | 3.0 |

The above-described acrylic type pressure-sensitive adhesive (TS-620) was spread over a removably treated film so that the thickness after drying is approximately 50 $\mu$m, and organic solvent is removed. A circular fine quality paper 5 cm$^2$ in surface area is laminated to the adhesive, and porous material is laminated thereon. 0.5 g o the medicine independently prepared are added dropwise to the porous material on which the fine quality paper is laminated and then is heatsealed with a backing layer to form a heatsealed laminate. The laminate thus obtained is cut in the shape of circle 20 cm$^2$ in surface area so as to position the heatseal at center to prepare a specimen Comparative example 2

| | |
|---|---|
| acrylic type pressure-sensitive adhesive (TS-620: trade name for Nippon Carbide Co., Ltd.) | 97.0 solid content |
| ondansetron hydrochloride | 3.0 |

All components are dissolved in an organic solvent such as hexane, toluene, ethyl acetate and so forth, then were spread over a substrate, and thereafter coated with a liner after removing the solvent to form a laminate. A specimen in desired shape is cut out of the laminate thus prepared. Alternatively, all components are dissolved in an organic solvent such as hexane, toluene, ethyl acetate and so forth, then were spread over a removably treated film, ad thereafter were pressed to a proper substrate to transfer thereon to obtain a specimen.

Comparative Example 3

| | |
|---|---|
| styrene-isoprene-styrene block copolymer | 25.0 |
| polyisobutylene | 5.0 |
| liquid paraffin | 42.0 |
| tackifier (alicyclic saturated hydrocarbon resin) | 25.0 |
| ondansetron hydrochloride | 3.0 |

A specimen was prepared in a Tanner similar to that of Comparative Example 2.

Comparative Example 4

Estraderm TTS (available from Ciba Specialty Chemicals Inc, formerly Ciba Geigy Ltd.)

Comparative example 4

Nitroderm TTS (available from Ciba Specialty Chemicals Inc. formerly Ciba Geigy Ltd.)

[Test Example]

Test Example 1

Adhesion Test

Adhesive test and skin irritation test were carried out in a manner describe below to each specimen of Examples and the specimens of Comparative Examples 1 and 4 as well as 5. The specimens were patched to brachia of 20 investigational persons, (health, male) to evaluate after 72 hours The results obtained were, shown in Tables 1 and 2. In comparative Examples 4 and 5, more than ½-release were observed in most of investigational persons after 72 hours patch test in Comparative Example 1, ¼-release were observed in most of investigational persons, in contrast, no release was observed in most of investigational persons in Examples. With respect to shin irritation, obvious erythemata (red spots )were observed in most of investigational persons, in contrast, extremely light erythemata (red spots )were observed in Examples.

TABLE -1

| investigational person | Example 1 | Example 2 | Example 3 | Com. Ex. 1 | Com. Ex. 2 | Ref. Ex. 1 |
|---|---|---|---|---|---|---|
| A | 5 | 5 | 5 | 1 | 3 | 2 |
| B | 5 | 4 | 5 | 0 | 1 | 2 |
| C | 5 | 4 | 5 | 2 | 1 | 3 |
| D | 5 | 4 | 5 | 1 | 2 | 2 |
| E | 5 | 5 | 5 | 2 | 2 | 3 |
| F | 5 | 4 | 5 | 2 | 1 | 3 |
| G | 5 | 4 | 5 | 1 | 2 | 3 |
| H | 4 | 5 | 4 | 2 | 2 | 3 |
| I | 5 | 4 | 5 | 2 | 2 | 3 |
| J | 5 | 5 | 5 | 3 | 2 | 4 | release: 0
¾ release: 1
½ release: 2
¼ release: 3
release of edge: 4
no release: 5

TABLE-2

| | 30 minutes after removal | | | | | | | 24 hours after removal | | | | | | |
|---|---|---|---|---|---|---|---|---|---|---|---|---|---|---|
| | Ex. 1 | Ex. 2 | Ex. 3 | C.E 1 | C.E 2. | R.E 1 | R.E 2 | Ex. 1 | Ex. 2 | Ex. 3 | C.E 1 | C.E 2 | R.E 1 | R.E 2 |
| A | 1 | 0 | 1 | 3 | 2 | 3 | 3 | 0 | 0 | 0 | 2 | 1 | 2 | 3 |
| B | 0 | 1 | 0 | 3 | 2 | 2 | 3 | 0 | 0 | 0 | 2 | 2 | 2 | 2 |
| C | 1 | 0 | 1 | 2 | 2 | 3 | 3 | 0 | 0 | 0 | 2 | 2 | 1 | 2 |
| D | 1 | 0 | 0 | 3 | 3 | 2 | 3 | 0 | 0 | 0 | 3 | 2 | 1 | 3 |
| E | 0 | 1 | 1 | 3 | 2 | 3 | 3 | 0 | 0 | 0 | 3 | 2 | 2 | 2 |
| F | 0 | 1 | 0 | 2 | 2 | 2 | 3 | 0 | 0 | 0 | 2 | 1 | 2 | 2 |
| G | 0 | 1 | 0 | 3 | 2 | 3 | 3 | 0 | 0 | 0 | 2 | 2 | 2 | 2 |
| H | 0 | 0 | 1 | 2 | 2 | 2 | 3 | 0 | 0 | 0 | 2 | 2 | 1 | 2 |
| I | 0 | 0 | 0 | 2 | 2 | 3 | 3 | 0 | 0 | 0 | 2 | 1 | 2 | 2 |
| J | 1 | 0 | 0 | 3 | 2 | 3 | 2 | 0 | 0 | 0 | 2 | 2 | 2 | 3 | no erythemata (red spots): 0
extremely light erythemata (red spots): 1
remarkable erythemata (red spots): 2
medium or strong erythemata (red spots): 3
Ex.: Example
C.E.: Comparative Example
R.E.: Reference Example

Test Example 2

Stability Test

Each specimen of Examples and Comparative examples was preserved at 50° C. for three months to confirm change in weight of each specimen and oozing of medicine therefrom.

The specimen the change in weight of which was more than 10% was marked with, the remainder of the specimen were marked with ○. With respect to oozing of medicine, the specimen to the liner of which the medicine was adhered when releasing the liner was marked with X, and the remainder of the specimen were marked with ○.

The results obtained were shown in Table-3 The change in weight and oozing of medicine were X in comparative Example 1, but, in contrast, they were ○ in Examples.

TABLE 3

| | Example 1 | Example 2 | Example 3 | Ref. Example 1 |
|---|---|---|---|---|
| Change in weight | ○ | ○ | ○ | x |
| oozing of medicine | ○ | ○ | ○ | x |

Test Example 3
Cohesive Force Test

Each of specimen of Examples and Comparative Examples 4 and 5 was stuck to a stainless steel plate, and was allowed to stand for the then being, and thereafter each of specimen was removed slowly by fingers. The state at the time of removing was observed. Evaluation was carried out as follows A stainless steel plate on the surface of which the adhesive was remained was marked with X, and the stainless steel plate on the surface of which the adhesive was not remained was marked with ○, and further the stainless steel plate with cobwebbing was marked with X, and the stainless steel without cobwebbing was marked with ○. The results obtained were shown in Table4. The remaining adhesive and cowebbing were not absolutely observed in Examples, but, in contrast, cowebbing was observed in all specimens of Comparative Examples 4 and 5.

TABLE 4

|  | Example 1 | Example 2 | Example 3 | Comparative Example 1 | Comparative Example 2 |
|---|---|---|---|---|---|
| remains of adhesive | ○ | ○ | ○ | X | X |
| cowebbing | ○ | ○ | ○ | X | X |

Test Example 4.
Penetration Test for Hairless Mouse Skin

Figure 3:
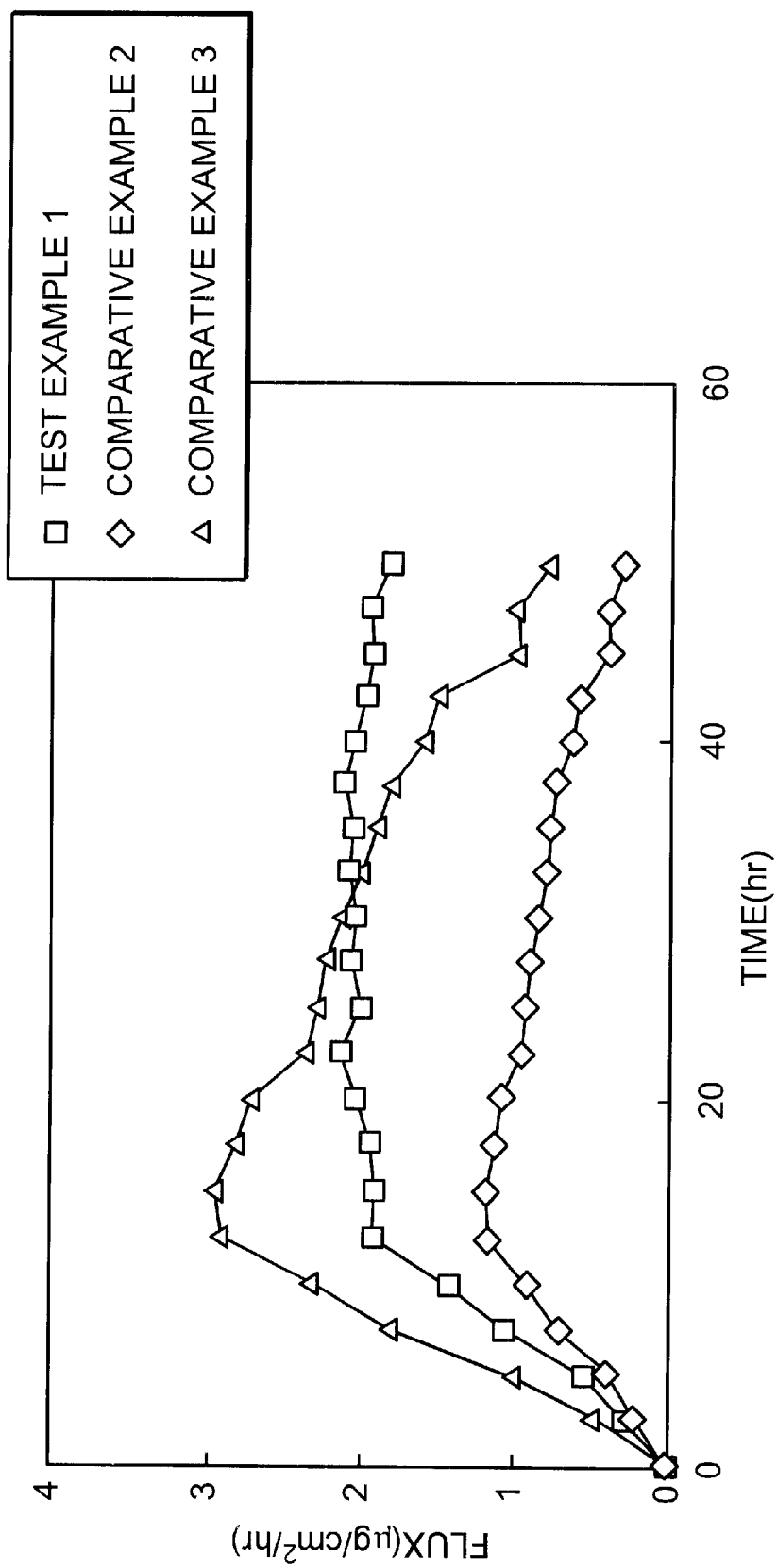
FIG. 3 is a graph showing a result of Skin permeability test using the percutaneous-absorbable pharmaceutical preparation of Example 1 of this invention and test specimens of Comparative Examples 2 and 3.

Skin penetration tests were carried out for specimens of Reference Examples and Examples. Skin of back of a hairless mouse (age: six weeks, male) was forced into a Franz-type diffusion cell and each specimen was attached to upper surface of the skin, and the temperature of a receptor layer was maintained at 37° C., and sampling was cared out by 1 ml every predetermined time over 50 hours. And, sampling solution was measured by means of high performance liquid chromatography. The results obtained were shown in FIG. 3. One-dimensional release was obtained in the specimens of Reference Examples 2 and 3, but in contrast, zero-dimensional release in which release was controlled was obtained in the specimens of Examples.

Industrial Applicability

The percutaneous therapeutic apparatus containing serotonin-receptor antagonist of this invention can get rid of, during preservation of the apparatus, lowering of adhesion resulted from an interaction with medicine and increase of skin irritation accompanying with enlargement of bulk caused by placing a pressure-sensitive layer on the periphery of the apparatus, and, when using the apparatus, can supply an effective amount of drug from a liquid medicine storage layer through a medicine-releasing layer to skin surface and to control release of medicine by virtue of the pressure-sensitive layer covering the whole surface of the medicine-releasing layer.

And, further the percutaneous therapeutic apparatus containing serotonin-receptor antagonist and the percutaneous absorption pharmaceutical preparation of this invention is able to administer drugs stably over a long period of time.

What is claimed is:

1. A percutaneous therapeutic apparatus having at least three layers comprising;
   (A) a backing layer,
   (B) a medicine storage layer consisting essentially of a liquid or semisolid composition comprising a serotonin-receptor antagonist, a lower alcohol, and water, and
   (C) a medicine-releasing layer, the whole surface of which is covered by a pressure-sensitive adhesive layer which controls the release of medicine,
   wherein said pressure-sensitive adhesive layer is comprised of rubber elastomer, tackifier, and softening agent, and
   wherein the medicine storage layer is positioned between said backing layer and the medicine-releasing layer.

2. A percutaneous therapeutic apparatus having at least three layers comprising:
   (A) a backing layer,
   (B) a medicine storage layer consisting essentially of a liquid or semisolid composition comprising a serotonin-receptor antagonist, a lower alcohol, and water, and
   (C) a medicine-releasing layer, the whole surface of which is covered by a pressure-sensitive adhesive layer which controls the release of medicine,
   wherein said pressure-sensitive adhesive layer is comprised of rubber elastomer, tackifier, softening agent, and acrylic type pressure-sensitive adhesive, and
   wherein the medicine storage layer is positioned between said backing layer and the medicine-releasing layer.

3. A percutaneous therapeutic apparatus described in claim 1 or 2, further comprising a removable release liner positioned such that said medicine-releasing layer is between said removable release liner and said medicine storage layer.

4. A percutaneous therapeutic apparatus described in claim 1 or 3, wherein said medicine-releasing layer is a medicine-permeable film, the whole surface of which is covered by a pressure-sensitive adhesive layer which controls the release of medicine.

5. A percutaneous therapeutic apparatus described in claim 2, wherein said pressure-sensitive adhesive layer is comprised of 5–50 weight percent of rubber elastomer, 5–50 weight percent of tackifier, 10–70 weight percent of softening agent and 0–80 weight percent of acrylic type pressure-sensitive adhesive on the basis of total weight of said pressure-sensitive adhesive layer.

6. A percutaneous therapeutic apparatus described in claim 4, wherein said medicine-permeable film comprises one or more than one of a porous film.

7. A percutaneous therapeutic apparatus described in claim 1 or 2, wherein said medicine in said medicine storage layer contains 10–40 weight percent of lower alcohol, 20–40 weight percent of wetting agent, 20–70 weight percent of water, 1–10 weight percent of irritation-reducing agent and 0.1–10 weight percent of absorption enhancer.

8. A percutaneous therapeutic apparatus described in claim 1 or 2, wherein the thickness of said pressure-sensitive adhesive layer is from about 30 $\mu$m to about 300 $\mu$m.

9. A percutaneous therapeutic apparatus described in claim 4, wherein said medicine-permeable film has 10–500 sec/100 cc of Gurley permeability.

10. A percutaneous therapeutic apparatus described in claim 1 or 2, wherein the backing layer and pressure-sensitive adhesive layer are sealed about the periphery of the medicine-releasing layer.

11. A percutaneous therapeutic apparatus having at least three layers comprising:
   (A) a backing layer,
   (B) a medicine storage layer consisting essentially of a liquid or semisolid composition comprising a serotonin-receptor antagonist, a lower alcohol, wetting agent, water, irritation-reducing agent and absorption enhance, and (C) a medicine-releasing layer, the whole surface of which is covered by a pressure-sensitive layer which controls the release of medicine, wherein said pressure-sensitive adhesive layer is comprised of rubber elastomer, tackifier, and softening agent, and wherein the medicine storage layer is positioned between said backing layer and the medicine-releasing layer.

12. A percutaneous therapeutic apparatus having at least three layers comprising:

(A) a backing layer, (B) a medicine storage layer consisting essentially of a liquid or semisolid composition comprising a serotonin-receptor antagonist, a lower alcohol, wetting agent, water, irritation-reducing agent and absorption enhance, and (C) a medicine-releasing layer, the whole surface of which is covered by a pressure-sensitive adhesive layer which controls the release of medicine, wherein said pressure-sensitive adhesive layer is comprised of rubber elastomer, tackifier, softening agent, and acrylic type pressure-sensitive adhesive, and wherein the medicine storage layer is positioned between said backing layer and the medicine-releasing layer.

* * * * *